United States Patent [19]

Weber et al.

[11] 4,201,712
[45] May 6, 1980

[54] PROCESS FOR PREPARATION OF 6-ARYL-4H-S-TRIAZOLO-[3,4-C]-THIENO-[2,3-E]-1,4-DIAZEPINES

[75] Inventors: Karl-Heinz Weber, Gau-Algesheim; Adolf Bauer; Adolf Langbein, both of Ingelheim am Rhein, all of Fed. Rep. of Germany

[73] Assignee: Boehringer Ingelheim GmbH, Ingelheim am Rhein, Fed. Rep. of Germany

[21] Appl. No.: 783,143

[22] Filed: Mar. 31, 1977

Related U.S. Application Data

[63] Continuation-in-part of Ser. No. 704,845, Jul. 13, 1976, abandoned.

[30] Foreign Application Priority Data

| Jul. 16, 1975 | [DE] | Fed. Rep. of Germany | 2531677 |
| Jul. 16, 1975 | [DE] | Fed. Rep. of Germany | 2531678 |
| Jul. 16, 1975 | [DE] | Fed. Rep. of Germany | 2531679 |
| Jul. 30, 1975 | [DE] | Fed. Rep. of Germany | 2533924 |

[51] Int. Cl.² .......... C07D 495/14; C07D 495/04; C07D 409/04; C07D 333/36
[52] U.S. Cl. .......... 260/244.4; 260/239.3 B; 424/232; 424/267; 424/269; 548/262
[58] Field of Search .......... 260/308 R, 293.57, 308 R, 260/244.4

[56] References Cited

U.S. PATENT DOCUMENTS

| 3,598,808 | 8/1971 | Szmuszkovicz | 260/239.3 R |
| 3,904,641 | 9/1975 | Nakanishi et al. | 260/308 R |

*Primary Examiner*—Alton D. Rollins
*Attorney, Agent, or Firm*—Hammond & Littell, Weissenberger & Muserlian

[57] ABSTRACT

A multiple-step process for the preparation of 6-aryl-4H-s-triazolo-[3,4-c]-thieno-[2,3-e]-1,4-diazepines of the formula

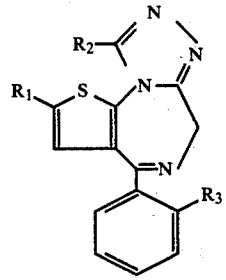

wherein
$R_1$ is hydrogen, halogen or lower alkyl of 1 to 2 carbon atoms;
$R_2$ is hydrogen, chlorine, bromine, straight or branched alkyl of 1 to 3 carbon atoms, ω-hydroxyalkyl of 1 to 3 carbon atoms, cycloalkyl of 3 to 6 carbon atoms or a 5- or 6-membered heterocycle comprising an oxygen sulfur or nitrogen atom, where the nitrogen atom may optionally be substituted by lower alkyl; and
$R_3$ is hydrogen, fluorine, chlorine, or bromine;
and optionally acid addition salts thereof, starting from compounds of the formula

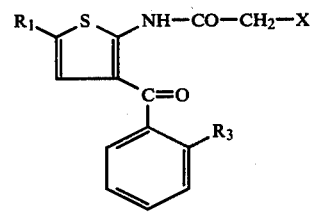

wherein
$R_1$ and $R_3$ have the meanings defined above, and
X is halogen, amino or acyloxy.

6 Claims, No Drawings

PROCESS FOR PREPARATION OF 6-ARYL-4H-S-TRIAZOLO-[3,4-C]-THIENO-[2,3-E]-1,4-DIAZEPINES

This is a continuation-in-part of copending application Serial No. 704,845 filed July 13, 1976, now abandoned.

This invention relates to a novel process for the preparation of certain 6-aryl-4H-s-triazolo-[3,4-c]thieno-[2,3-e]-1,4-diazepines, as well as to certain intermediate products formed in the course of the process.

More particularly, the present invention relates to a novel process for the preparation of 6-aryl-4H-s-triazolo-[3,4-c]-thieno-[2,3-e]-1,4-diazepines of the formula

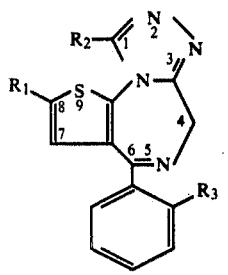

(VII)

wherein $R_1$ is hydrogen, halogen or lower alkyl of 1 to 2 carbon atoms;

$R_2$ is hydrogen, chloride, bromine, straight or branched alkyl of 1 to 3 carbon atoms, ω-hydroxyalkyl of 1 to 3 carbon atoms, cycloalkyl of 3 to 6 carbon atoms or a 5- or 6-membered heterocycle comprising an oxygen, sulfur or nitrogen atom, where the nitrogen atom may optionally be substituted by lower alkyl; and $R_3$ is hydrogen, fluorine, chlorine or bromine;

and optionally acid addition salts thereof, which comprises the steps of (a) reducing a compound of the formula

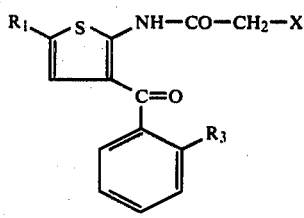

(I)

wherein $R_1$ and $R_3$ have the meanings defined above, and

X is halogen, amino or acyloxy by means of sodium borohydride in dimethylformamide or dimethylacetamide at temperatures between 0° and +10° C. to form a corresponding carbinol of the formula

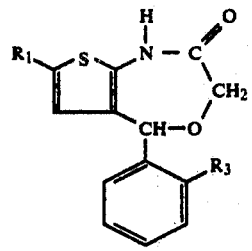

(Ia)

wherein $R_1$, $R_3$ and X have the meanings defined above;

(b) treating the carbinol, optionally after conversion of the amino group into a halogen atom or after splitting off the acyl group, with a suitable cyclization agent to form a carbonyl compound of the formula

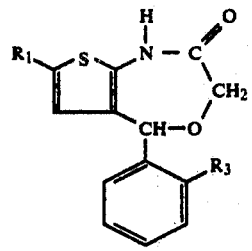

(II)

wherein $R_1$ and $R_3$ have the meanings defined above, (c) converting the carbonyl group into the mercapto, a lower alkoxy or an alkylmercapto group or into a halogen atom by conventional methods to form a compound of the formula

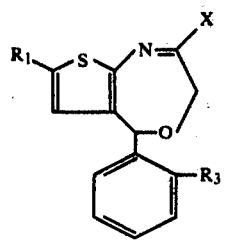

(III)

wherein $R_1$ and $R_3$ have the meanings defined above, and

X is SH—, lower alkoxy, alkylmercapto or halogen, (d) reacting the compound thus obtained with a compound of the formula $$R_2-CO-NH-NH_2 \qquad (IV)$$

wherein $R_2$ has the meaning previously defined except chlorine and bromine, (e) optionally chlorinating or brominating the resulting compound of the formula

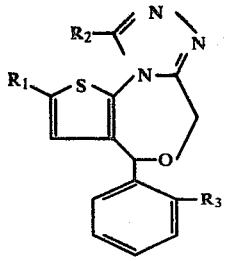

(V)

wherein $R_1$ and $R_3$ have the meanings defined above and $R_2$ is hydrogen, (f) cleaving the oxazepine ring of the compound of formula V at the oxygen atom by treating it with a strong hydrohalic acid, (g) extracting the resulting hydrohalide of a compound of the formula

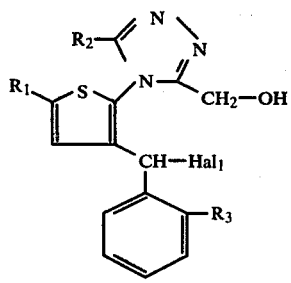

(Va)

wherein
$R_1$ through $R_3$ have the meanings defined above and $Hal_1$ is halogen,
with a water-immiscible solvent and evaporating the extract solution, (h) admixing the residue with a phosphorus halide or sulfur halide, (i) reacting the resulting dihalo compound of the formula

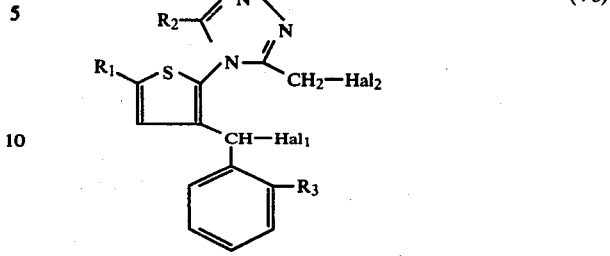

(Vb)

wherein
$R_1$ through $R_3$ have the meanings defined above, and $Hal_1$ and $Hal_2$ are halogen,
with ammonia or an ammonia-releasing substance to form a compound of the formula

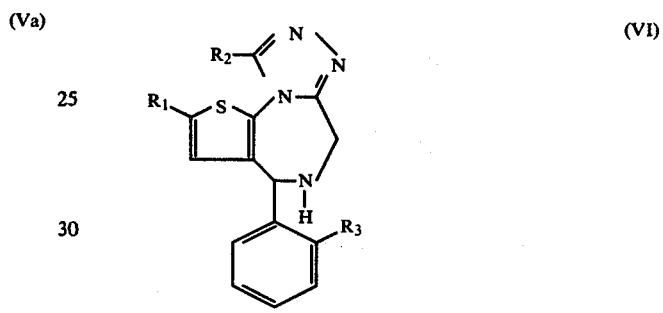

(VI)

wherein $R_1$ through $R_3$ have the meanings defined above, and (j) dehydrogenating the resulting compound by conventional methods, and optionally converting the dehydrogenated compound into a physiologically acceptable acid addition salt thereof.

The process of the present invention can be schematically represented by the following flow diagram:

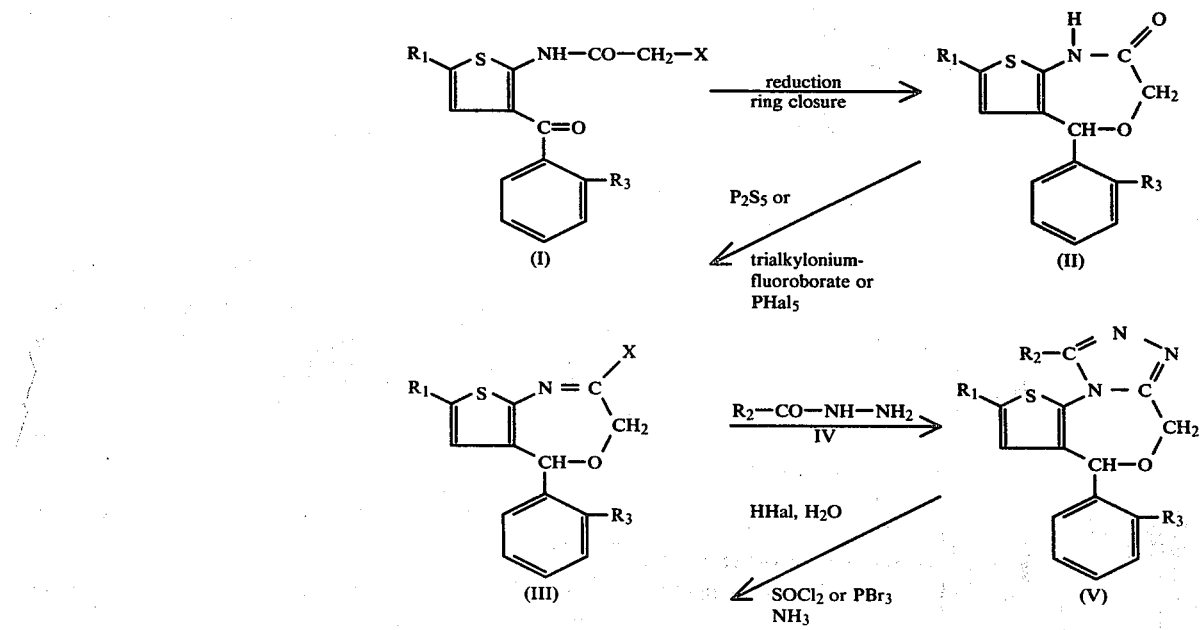

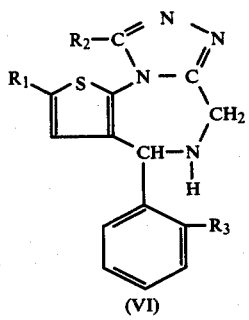

(VI)

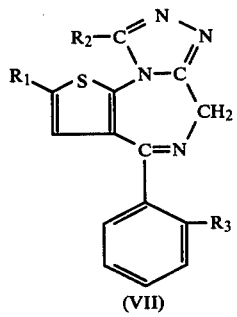

(VII)

dehydrogenation

The compounds of the formulas II, III, V and VI are new.

Starting from the same starting compound, that is, from a 2-haloacetamido-3-benzoylthiophene of the formula I, the conventional process for the preparation of thieno-triazolo-diazepines proceeds via the corresponding amine, cyclization to form the diazepinone, activation of the carbonyl group, and reaction with a hydrazine derivative to the desired end product. Although this conventional synthesis involves two steps less than the process according to the invention, the latter produces an over-all yield which is nearly twice as high as the yield obtained in the conventional process. We have determined that the formation of the triazolo ring is the critical step in the synthesis of the end product. Probably for steric reasons, this ring closure proceeds on the oxazepine molecule spontaneously and nearly quantitatively, whereas the corresponding cyclization on the diazepine molecule requires a longer time and in most cases a high reaction temperature.

In the synthesis of the thieno triazolo diazepines pursuant to the present invention a ketone of the formula

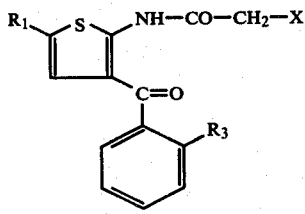

(I)

wherein
  $R_1$ and $R_3$ have the meanings defined above, and
  X is halogen, amino or acyloxy,
is first reduced to the corresponding carbinol of the formula

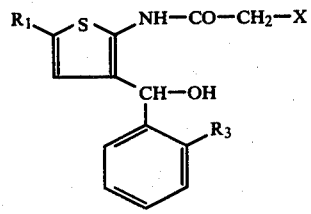

(Ia)

wherein $R_1$, $R_3$ and X have the meanings defined above, if necessary converting the amino group into a halogen atom or splitting off the acyl group, followed by cyclization which yields a thieno oxazepine of the formula

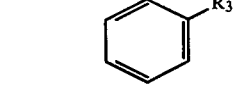

(II)

wherein $R_1$ and $R_3$ have the meanings defined above.

The reduction of the ketone I to the carbinol Ia is effected according to the invention by means of sodium borohydride in dimethylformamide or dimethylacetamide at low temperature, preferably between 0° and +10° C. Surprisingly, there occurs during this procedure scarcely any reductive cleavage of radical X or a hydrolytic cleavage of radical —CO—CH$_2$—X, while in other solvents, for example in a lower alcohol, the cleavage reactions predominate over the carbinol formation.

If X in formula I is amino, it is converted subsequent to the reductiion into the corresponding halocarbinol by reaction with nitrous acid in strong hydrohalic acid solution.

If X is an acyloxy group, it is split off with a strong alkali after the reduction with sodium borohydride.

The detour via a functional derivative of the aminoketone proved to be necessary in the present case because, as we surprisingly discovered, unlike the easily reducible 2-aminobenzophenones (see, for example, German Offenlegungsschrift No. 15 45 639) the corresponding 2-aminobenzoylthiophenes cannot be reduced directly to the carbinols.

The carbinol Ia is obtained in the manner described above is, in contrast to the keto compounds I which are sensitive to hydrolysis, surprisingly extremely stable against alkalis, a circumstance to which the high yields of the sodium borohydride reduction described above are ascribed.

The cyclization of the carbinol Ia to the oxazepine of the formula II following the reduction is effected, in case X is halogen, with a suitable alkali metal alcoholate or with sodium hydride; sodim isopropylate and sodium tert. butylate are preferred for the cyclization. Suitable solvents are alcohols, tetrahydrofuran, dioxane, dimethylformamide or inert solvents, such as benzene or its homologues. The reaction temperature depends upon the starting material used in each case and lies between 0° C. and the boiling point of the particular solvent which is employed.

In case X is —OH, the cyclization succeeds with the conventional dehydrating agents, such as thionyl chloride, sulfuric acid, polyphosphoric acid or dicyclohexylcarbodiimide.

The introduction of substituent $R_1$ may be effected at any stage of the reaction sequence.

In case $R_1$ represents a lower alkyl group, it is advantageous if this group is already present during construction of the thiophene ring.

On the other hand, halogen atoms may already be introduced at the stage of the acylaminoketone I, or else into a compound of the formula II. Halogenation is effected in both cases within a short time by reaction with the equivalent quantity of the halogen or a suitable halogen compound, such as sulfuryl halide or halosuccinimide or the like, in solvents such as carbon tetrachloride, chloroform, methylene chloride, dioxane, tetrahydrofuran, dimethylformamide or a suitable hydrocarbon, optionally in the presence of a tertiary organic base, for example pyridine. The reaction temperature during the halogenation lies, depending upon the starting material which is used and the method which is applied, between room temperature and the reflux temperature of the reaction mixture.

The starting compounds of the formula I are known from the literature and may be obtained in accordance with the method described in "Monatsheften der Chemie" 104, 704 (1973).

The compounds of the formula II are useful as intermediates for the production of therapeutically useful substituted thieno-[2,3-e]-triazolo-[3,4-c]-1,4-diazepines (VII). Such compounds are disclosed in abandoned U.S. applications Ser. No. 554,309 filed Feb. 28, 1975, Ser. Nos. 672,280 and 672,281 filed Mar. 31, 1976, as well as in German Offenlegungsschrift No. 2,229,845.

These compounds of the formula VII are obtained, starting from the above-mentioned intermediates, by reaction with a carboxylic acid hydrazide whereby the corresponding thieno-[2,3-e]-triazolo-[3,4-c]-4,1-oxazepine is formed, opening of the oxazepine ring with hydrohalic acids, conversion of the thus formed 4-(3-phenyl-halomethyl)-thienyl-(2)-5-hydroxymethyl-1,2,4-triazole into the corresponding 5-halomethyl compound, cyclization with ammonia and dehydrogenation.

The above-mentioned compounds of the formula II are reacted with phosphorus pentasulfide in a solvent, such as dimethylformamide, diglyme or tetrahydrofuran, and preferably in the presence of an alkali metal carbonate, pyridine or mixtures thereof. The temperatures used for this purpose may lie between room and reflux temperature of the reaction mixture. Thus, compounds of the formula

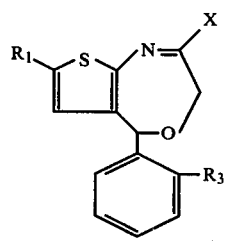

(III)

wherein $R_1$ and $R_3$ have the previously indicated meanings, and X is —SH are obtained.

They exist in tautomeric equilibrium with the corresponding thiono compounds:

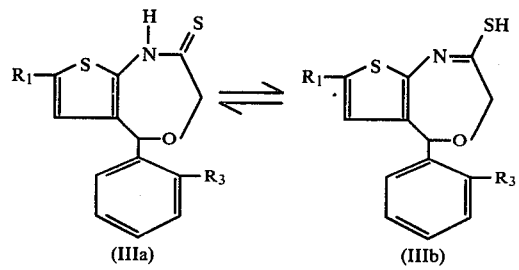

(IIIa)           (IIIb)

These compounds may, after reaction with sodium methylate or sodium amide in a solvent to form the corresponding salts, be reacted without previous separation in the usual way with alkylation agents, such as methyl or higher alkyl iodide, to form compounds of the formula III where X is a lower alkylthio group.

Compounds of the formula III, where X is a lower alkoxy group, are obtained from compounds of the formula II by reaction with a trialkyloxonium fluoroborate. The latter compound, obtained in accordance with a process described by H. Meerwein et al in J.pr.Chem. (2), 147, 257 (1937) and 154, 83 (1939) from borontrifluoride etherate and epichlorohydrin, is reacted in situ with a compound of the formula II.

Suitable solvents are especially ethers or halogenated hydrocarbons, such as carbon tetrachloride. The reaction temperature lies in general between 0° C. and the boiling point of the particular solvent which is used.

Compounds of the formula III where X is halogen are produced by treating a compound of the formula II with an inorganic acid halide, preferably phosphorus pentachloride, in an anhydrous organic solvent, such as dioxane or tetrahydrofuran, at temperatures between −50° and +50° C. The imide-chloride thus obtained may be reacted in situ with compounds of the formula IV to form the triazolo thieno oxazepine V. In special cases, however, the halogen compound can be isolated too.

Compounds of the formula III are then reacted with a compound of the formula $$R_2\text{—CO—NH—NH}_2 \qquad (IV)$$

wherein $R_2$ is hydrogen, straight or branched alkyl of 1 to 3 carbon atoms, ω-hydroxyalkyl of 1 to 3 carbon atoms, cycloalkyl of 3 to 6 carbon atoms or a 5- or 6-membered saturated heterocycle comprising an oxygen, sulfur or nitrogen atom, where the nitrogen heteroatom may optionally be substituted by lower alkyl, whereby a compound of the formula

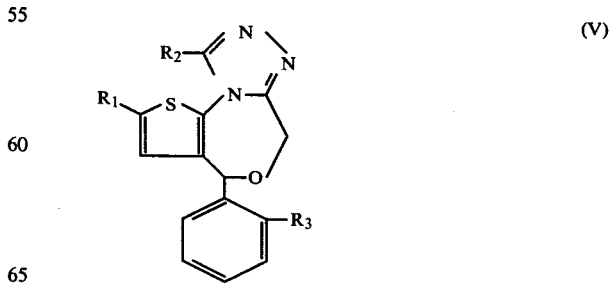

(V)

where $R_1$ through $R_3$ have the previously indicated meanings, is obtained.

This reaction may be effected at temperatures between 100° and 250° C. without a solvent, as well as in a solvent such as methanol, ethanol, dioxane, chloroform, tetrahydrofuran, benzene, toluene, xylene or mixtures of these, in the absence or presence of an acid catalyst, such as hydrochloric acid, sulfuric acid, phosphoric acid, polyphosphoric acid, acetic acid, propionic acid, benzenesulfonic acid or toluenesulfonic acid; the intermediate product formed during this reaction, namely

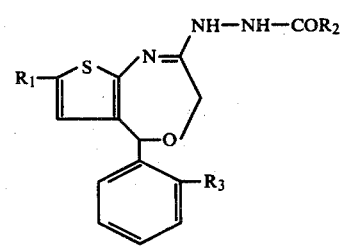

(IIIc)

where $R_1$ through $R_3$ have the meanings defined above, is not isolated.

For production of those end products of the formula V where $R_2$ is chlorine or bromine, a compound of the formula V where $R_2$ is hydrogen, is brominated or chlorinated. The halogenation is effected in a solvent, such as carbon tetrachloride, chloroform, methylenechloride, dioxane, tetrahydrofuran, dimethylformamide or a suitable hydrocarbon, optionally in the presence of a tertiary organic base, such as pyridine, or else by means of a halosuccinimide. For this reaction the temperature lies between room and reflux temperature of the reaction mixture, depending upon the particular starting material and the method which is used.

Starting from the thieno-[2,3-e]-triazolo-[3,4-c]-4,1-oxazepines of the formula V, the thieno triazolo diazepines of the formula VI are obtained pursuant to the following reaction sequence:

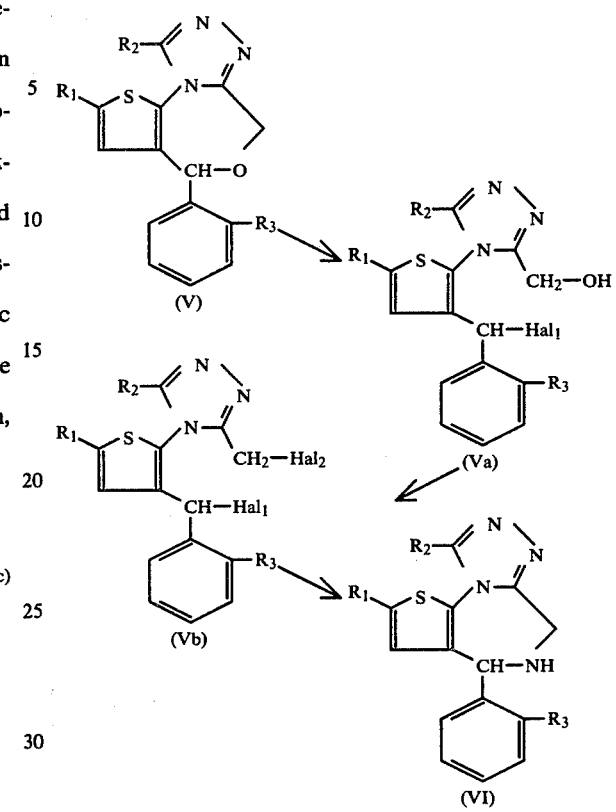

Thus, the oxazepine ring of a compound of the formula V is cleaved at the oxygen atom by treatment with strong hydrochloric acid or hydrobromic acid. For this purpose it suffices in general to let a compound of formula V stand in strong hydrochloric or hydrobromic acid solution from several minutes up to several hours at room temperature.

The hydrohalide of a compound of the formula Va formed thereby is extracted from the cold reaction solution with a water-immiscible solvent, preferably a chlorinated hydrocarbon, such as chloroform or methylene chloride, and, advantageously after evaporation of the extract solution, admixed with a phosphorus or sulfur halide, such as thionyl chloride or phosphorus tribromide. The reaction temperature lies here between 0 and 40, preferably at about 20° C.

After distilling off the excess halide and, if required, the still present solvent, the residue consisting of a dihalide of the formula Vb is reacted with ammonia or a substance which release ammonia, such as urotropine. Suitable solvent for the reaction with ammonia are lower alcohols, such as methanol or ethanol, ethylacetate, dioxane, tetrahydrofuran or inert hydrocarbons, such as benzene and its homologues; but liquid ammonia may be used for the reaction as well. The reaction temperature lies between 0° C. and the boiling point of the particular solvent which is used; however, the reaction is preferably effected in an autoclave. The end products of the formula VI are obtained with excellent yields.

Instead of using a compound of the formula Va, the reaction with a phosphorus or sulfur halide may be effected as well with a corresponding dihydroxy compound of the formula

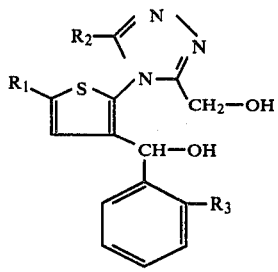
(Vc)

It is obtained by heating a strongly acid solution of a compound of formula V and it may be extracted from the reaction solution in the same manner as described for the compounds of formula Va.

The dehydrogenation of a compound of the formula VI to the desired end product of the formula VII is effected by using a suitable dehydrogenation agent, such as a halogen or a compound of the higher oxidation stage of chromium or manganese, for example a chromate, a bichromate or a permanganate. Examples of suitable solvents for the reaction with a halogen are chlorinated hydrocarbons, such as chloroform or methylene chloride; advantageously, this reaction is performed in the presence of a tertiary organic base, such as pyridine, to bind the hydrohalic acid which is released.

The oxidation with a compound of chromium or manganese is effected in a solvent, such as acetone, tetrahydrofuran or dioxane. Depending upon the type of oxidation agent which is employed, the reaction temperature lies in general between 0° C. and the boiling point of the particular solvent which is used.

If $R_2$ in a compound of the formula VI is hydrogen, the reaction with chlorine or bromine yields an end product of the formula VII where $R_2$ is hydrogen, or, if an excess of the halogen is used, an end product of the formula VII where $R_2$ is chlorine or bromine.

The end products of the formula VII form acid addition salts. Examples of non-toxic, pharmaceutically acceptable acid addition salts are those formed with hydrohalic acids, sulfuric acid, phosphoric acid, succinic acid, cyclohexylsulfaminic acid, citric acid, tartaric acid, ascorbic acid, maleic acid, formic acid, salicyclic acid, methane- or toluenesulfonic acid, 8-chlorotheophylline or the like.

The end products of the formula VII as well as their acid addition salts exhibit pronounced anticonvulsive, anxiolytic and antiaggressive activities in the dose range of 0.1 to 3 mgm/kg with very low toxicity, as disclosed in the aforementioned abandoned U.S. applications Ser. Nos. 554,309, 672,280 and 672,281.

The following examples illustrate the present invention and will enable other skilled in the art to understand it more completely. It should be understood, however, that the invention is not limited solely to the particular examples given below.

EXAMPLE 1

8-Bromo-6-(O-chlorophenyl)-1-methyl-4H-s-triazolo-[3,4-c]-thieno-[2,3-e]-1,4-diazepine (A) (a) 1 Mol=314 gm of 2-chloroacetylamino-3-(o-chlorobenzoyl)-thiophene were dissolved in 500 ml of dimethylformamide, and the solution was gradually admixed at 0° C., while vigorously stirring, over a period of one hour with a total of 36 gm of pulverized sodium borohydride. Subsequently, the mixture was poured into 2 liters of ice water, whereby a greasy precipitate was formed. The aqueous phase was decanted, and the greasy substance was washed 2 to 3 times with water and was then taken up in methylene chloride. After drying of the methylene chloride phase and evaporating it, 300 gm of an oil were obtained, which solidified gradually and was recrystallized from methanol/ether. 294 gm (93.1% of theory) of 2-chloroacetylamino-3-[(o-chlorophenyl)hydroxymethyl]-thiophene, m.p. 118°-120° C., were obtained. For the subsequent cyclization step the oil may be used as such without crystallization.

(b) 0.8 Mol=253 gm of 2-chloroacetylamino-3-[(o-chlorophenyl)-hydroxymethyl]-thiophene, dissolved in 200 ml of isopropanol, were added to a boiling solution of 52 gm (2.25 mols) of sodium in 1.8 liters of isopropanol, and the mixture was refluxed for 5 minutes. Subsequently, the result-brownish suspension was poured into 1.5 liters of ice water, and the aqueous mixture was acidified with concentrated hydrochloric acid. The crystalline precipitate formed thereby was suction-filtered off and washed with water. Then the moist residue was dissolved in 2 liters of methylene chloride, the solution was dried with magnesium sulfate and evaporated, and the residue was recrystallized from methanol. 242 gm (87% of theory) of 5-(o-chlorophenyl)-thieno-[2,3-e]-4,1-oxazepinone-(1) of m.p. 175°-176° C. were obtained.

(B) 0.1 Mol=27.9 gm of 5-(chlorophenyl)-thieno-[2,3-e]-4,1-oxazepinone-(1) were dissolved in a mixture of 300 ml of chloroform and 8.5 ml of pyridine, and a solution of 5.5 ml of bromine in 50 ml of chloroform was added over a period of 10 to 15 minutes at room temperature. Decoloration took place immediately and a precipitate formed which was suction-filtered off and washed with ether. Yield of 7-bromo-5-(o-chlorophenyl)-thieno-[2,3-e]-4,1-oxazepinone: 30 gm (83% of theory), m.p. 178°-180° C. (decomp.).

(C) (a) 0.1 Mol=35.8 gm of 7-bromo-5-(o-chlorophenyl)-thieno-[2,3-e]-4,1-oxazepinone were heated with 350 ml of diglyme, 24 gm of $P_2S_5$ and 19 gm of $NaHCO_3$ for 30 minutes at 60° C. Subsequently, the reaction mixture was poured over about 1 liter of ice water, whereby a crystalline precipitate was formed, which was suction-filtered off, washed with water and dried. 37 gm=99% of theory of 7-bromo-5-(o-chlorophenyl)-thieno-[2,3-e]-4,1-oxazepine-2-thione were obtained M.p. from 200° C. (decomp.).

(b) 0.1 Mol=37.5 gm of 7-bromo-5-(o-chlorophenyl)-thieno-[2,3-e]-4,1-oxazepine-2-thione were dissolved in 370 ml of tetrahydrofuran, and the solution was admixed with 10 ml of hydrazine hydrate. After 5 minutes at room temperature the reaction was finished. The reaction solution was evaporated, the residue was taken up in methylene chloride, the solution was washed several times with water, and the methylene chloride phase was separated and evaporated. The residue was taken up in 200 ml of ethanol, the solution was admixed with 50 ml of o-triethyl acetate, the mixture was refluxed for 30 minutes and then evaporated in vacuo, and the residue was crystallized with ether. Yield of 8-bromo-6-(o-chlorophenyl)-1-methyl-thieno-[2,3-e]-triazolo-[3,4-c]-4,1-oxazepine: 34.5 gm=87% of theory, m.p. 146°-148° C.

(D) (a) 0.1 Mol=39.6 gm of 8-bromo-6-(o-chlorophenyl)-1-methyl-thieno-[2,3-e]-triazolo-[3,4-c]-4,1- oxazepine were suspended in 250 ml of concentrated hydrobromic acid. As soon as a clear solution had formed (after 15 to 20 minutes), it was diluted with 300 ml of ice water, and the aqueous mixture was extracted with methylene chloride. The methylene chloride phase was dried and evaporated, and the residue was crystallized with ether. 52 gm of 3-methyl-4-[3-(o-chlorophenyl-bromomethyl)-5-bromo-thienyl-(2)]-5-hydroxymethyl-1,2,4-triazole hydrobromide (94% of theory), m.p. 200° C. (decomp.), were obtained.

(b) 0.05 Mol=27.9 gm of the hydrobromide obtained in the previous step were stirred with 100 ml of thionyl chloride for 30 minutes at room temperature. Then, the excess thionyl chloride was distilled off in vacuo, the residue taken up in methylene chloride, and the solution was washed with ice water and with dilute ammonia. The dried methylene chloride phase was evaporated, and the residue was triturated with ether. Yield: 24.2 gm of 3-methyl-4-[3-(o-chlorophenylbromomethyl)-5-bromo-thienyl-(2)]-5-chloromethyl-1,2,4-triazole, m.p. 167°–169° C.

(c) 12.4 gm of the end product of the previous step were dissolved in 270 ml of methanol, and 100 ml of liquid ammonia were added. Subsequently, the mixture was heated for 30 minutes at 100° C. in an autoclave. The reaction mixture was evaporated, the residue was taken up in methylene chloride, the solution was washed with water, the methylene phase was dried and evaporated, and the residue was recrystallized from methanol. Yield of 8-bromo-6-(o-chlorophenyl)-1-methyl thieno-[2,3-e]-triazolo-[3,4-c]-5,6-dihydro-1,4-diazepine: 9.0 gm=91% of theory, m.p. 160°–162° C.

(E) 39.5 gm=0.1 mol of 8-bromo-6-(o-chlorophenyl)-1-methyl-4H-s-triazolo-[3,4-c]-thieno-[2,3-e]-5,6-dihydro-1,4-diazepine were dissolved in a mixture of 500 ml of methylene chloride and 15 ml of pyridine, and the solution was admixed over a period of 10 minutes, while stirring at room temperature, with a solution of 10 ml of bromine in 50 ml of methylene chloride. The resulting solution, which decolored immediately, was stirred for 30 minutes, and was then extracted several times with water, dried and evaporated, and the residue was recrystallized from ethanol, yielding 36.9 cm (94% of theory) of the compound of the formula

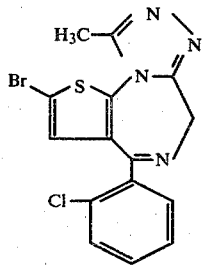

having a melting point of 208°–210° C.

Very good yields are obtained as well, if dehydrogenation is effected with potassium permanganate, as described in Example 3.

EXAMPLE 2

8-Bromo-6-(o-chlorophenyl)-1-[tetrahydropyranyl-(4)]-4H-s-triazolo-[3,4-c]-thieno-[2,3-e]-1,4-diazepine 0.01 mol=3.74 gm of 7-bromo-5-(o-chlorophenyl)-thieno-[2,3-e]-4,1-oxazepine-2-thione [see Example 1(C)(b)] were refluxed with 100 ml of dioxane and 1.5 gm of tetrahydropyrano-4-carboxylic acid hydrazide for 30 minutes. Then, the reaction mixture was worked up as described in Example 1 (C)(b). Yield of 8-bromo-6-(o-chlorophenyl)-1-[tetrahydropyranyl-(4)]-thieno-[2,3-e]-triazolo-[3,4-c]-4,1-oxazepine: 2.7 gm (58% of theory), m.p. 182°–184° C.

Analogous to the procedures described in Examples 1(D) and 1(E); the title compound was obtained via 8-bromo-6-(o-chlorophenyl)-1-[tetrahydropyranyl-(4)]-thieno-[2,3-e]-triazolo-[3,4-c]-5,6-dihydro-1,4-diazepine of m.p. 174°–175° C.; yield: 98% of theory; m.p. 257°–258° C.

EXAMPLE 3

8-Bromo-6-(o-chlorophenyl)-1-cyclohexyl-4H-s-triazolo-[3,4-c]-thieno-[2,3-e]-1,4-diazepine 4.65 gm=0.01 mol of 8-bromo-6-(o-chlorophenyl)-1-cyclohexyl-4H-s-triazolo-[3,4-c]-thieno-[2,3-e]-5,6-dihydro-1,4-diazepine (m.p. 192° C.), which had been obtained from 7-bromo-5-(o-chlorophenyl)-thieno-[2,3-e]-4,1-oxazepine-2-thione [see Example 1(C)(a); m.p. 200° C.] via 8-bromo-6-(o-chlorophenyl)-1-cyclohexyl-thieno-[2,3-e]-triazolo-[3,4-c]-4,1-oxazepine [see Example 1(C)(b); m.p. 172°–174° C.] according to the procedures described in Example 1(D)(a)–(c), were dissolved in 100 ml of acetone which had been freshly distilled over KMnO4. While boiling and stirring the resulting solution, first 3 gm of sodium bichromate in 15 ml of water and then 2 ml of 20% sulfuric acid were added, and boiling was continued for 30 minutes. The solvent was then distilled off, the residue was diluted with some water, made alkaline with ammonia and extracted with methylene chloride. After washing, drying and evaporating of the organic extract, the crude reaction product remained, which was recrystallized from ethanol. Yield: 4.1 gm=88% of theory; m.p. 190°–192° C.

Instead of sodium bichromate, potassium permanganate may also be used for the dehydrogenation. In that case the procedure is as follows:

4.65 gm=0.01 mol of 8-bromo-6-(o-chlorophenyl)-1-cyclohexyl-4H-s-triazolo-[3,4-c]-thieno-[2,3-e]-5,6-dihydro-1,4-diazepine are dissolved in a mixture of 50 ml of acetone and 50 ml of methylene chloride. 1.4 gm of finely pulverized KMnO4 is added all at once, and the mixture is stirred for 6 hours at room temperature. Manganese dioxide separates out. After suction filtration over diatomaceous earth, the light-yellow filtrate is evaporated, and the residue is triturated with ether. 4 gm=86% of theory of the title compound, m.p. 190°–192° C., are obtained.

EXAMPLE 4

1,8-Dibromo-6-(o-chlorophenyl)-4H-s-triazolo-[3,4-c]-thieno-[2,3-e]-1,4-diazepine 3.8 gm=0.01 mol of 8-bromo-6-(o-chlorophenyl)-4H-s-triazolo-[3,4-c]-thieno-[2,3-e]-5,6-dihydro-1,4-diazepine (m.p. 178° C.), which had been obtained from 7-bromo-5-(o-chlorophenyl)-thieno-[2,3-e]-4,1-oxazepine-2-thione via 8-bromo-6-(o-chlorophenyl)-thieno-[2,3-e]-triazolo-[3,4-c]-4,1-oxazepine (m.p. 182° C.) analogous to Example 1(D)(a)–(c), were dissolved in 50 ml of methylene chloride and 1 ml of pyridine. A solution of 1.5 ml of bromine in 15 ml of methylene chloride was added over a period of 10 minutes, and the mixed solution was then refluxed for 30 minutes. Thereafter, the reaction solution was washed with water, dried and evaporated. The resulting concentrate was chromatographed on a SiO₂-column and eluted with methylene chloride to which 2% of methanol had been added. The first main fraction contained 4.2 gm (92% of theory) of the title compound, m.p. 209°–210° C.

EXAMPLE 5

1,8-Dibromo-6-(o-chloro-phenyl)-4 H-s-triazolo-[3,4-c]-thieno-[2,3-e]-1,4-diazepine 6 gm (0.016 mol) of 8-bromo-6-(o-chloro-phenyl)-thieno-[2,3-e]-triazolo-[3,4-c]-4,1-oxazepine, m.p. 182° C. (see Example 4), were suspended in a mixture of 60 ml of methylene chloride and 1.9 gm of pyridine, and the suspension was admixed with a solution of 1.2 ml of bromine in 20 ml of methylene chloride. The resulting reaction mixture was stirred for three hours at 40° C. and was then diluted with 50 ml of methylene chloride and extracted several times with water. The methylene chloride phase was separated, the solvent was evaporated therefrom, and the residue was chromatographed on an SiO₂-column and eluted with methylene chloride containing 3% methanol. After recrystallization from methanol, 1,8-dibromo-6-(o-chloro-phenyl)-thieno-[2,3-e]-triazolo-[3,4-c]-4,1-oxazepine, m.p. 136°–138° C., was obtained. From this intermediate 1,8-dibromo-6-(o-chloro-phenyl)-4 H-s-triazolo-[3,4-c]-thieno-[2,3-e]-5,6-dihydro-1,4-diazepine, m.p. 175°–177° C., was obtained in a manner analogous to the procedures described in Example 1(D)(a)–(c). 4.6 gm (0.01 mol) of this compound were stirred for 15 hours at room temperature in 600 ml of acetone with 4 gm of potassium permanganate. Thereafter, the reaction mixture was diluted with 500 ml of methylene chloride, the precipitated manganese dioxide was separated by suction filtration, and the filtrate was evaporated. Upon addition of ether to the residue, the compound of the formula

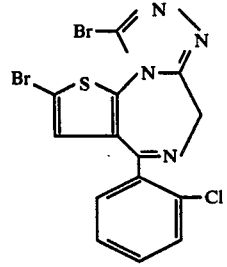

having a melting point of 209°–210° C. crystallized out. The yield was 3.6 gm (78% of theory).

Using procedures analogous to those of Examples 1–4, the end products of the formula VII shown in the following table were also prepared.

TABLE

| R₁ | R₂ | R₃ | m.p. °C. intermediate II | m.p. °C. intermediate V | m.p. °C. intermediate VI | m.p. °C. end product VII |
|---|---|---|---|---|---|---|
| Br | CH₃ | Br | 176 (decomp.) | 137–139 | 171–173 | 205–206 |
| Cl | CH₃ | Cl | 223–225 | 124–126 | 131–133 | 204–206 |
| Br | CH₃ | F | 145–150 (decomp.) | 170–171 | 180–182 | 208–210 |
| C₂H₅ | CH₃ | Cl | 148–150 | 90 | 120–122 | 144–146 |
| Br | CH₃ | Cl | 178–180 | 146–148 | 160–162 | 208–210 |
| Br | —⟨cyclohexyl-H⟩ | Cl | 178–180 | 172–174 | 190–192 | 190–192 |
| Br | —⟨tetrahydropyranyl-O⟩ | Cl | 178–180 | 182–184 | 174–175 | 257–258 |
| Br | —⟨cyclopropyl⟩ | Cl | 178–180 | 169–170 | 156–158 | 212–214 |
| Br | H | Cl | 178–180 | 182 | 176–178 | 198–200 |
| Br | —CH₂—OH | Cl | 178–180 | 198 | 205–206 | 224–225 |
| Br | Br | Cl | 178–180 | 135–137 | 135–137 (decomp.) | 209–210 |

| R₁ | R₂ | R₃ | Fp. °C. II | Fp. °C. V | Fp. °C. VI | Fp. °C. VII |
|---|---|---|---|---|---|---|
| Br | —⟨tetrahydropyranyl-O⟩ | Cl | 178–80 | 170–73 | — | 187–88 |
| Br | —⟨tetrahydropyranyl-O⟩ | Br | 176 (dec) | 178 | — | 242 |
| Br | —⟨tetrahydrofuranyl-O⟩ | Br | 176 (dec) | 165–167 | — | 140–41 |

TABLE-continued

| | | | | | |
|---|---|---|---|---|---|
| Br | (thiophene) | Cl 178–80 | 173–174 | — | 231–33 |
| Br | (CH₃—N piperidyl) | Cl 178–80 | oil | — | 241 |

We claim:

1. A process for the preparation of a 6-aryl-4 H-s-triazolo-[3,4-c]-thieno-[2,3-e]-1,4-diazepine of the formula

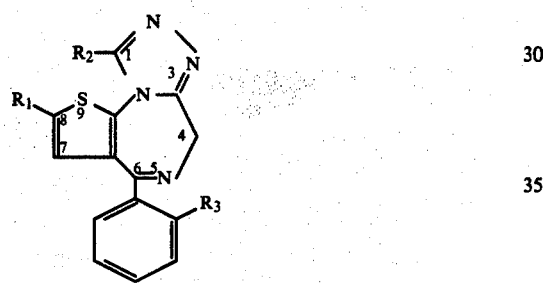

wherein
R₁ is hydrogen, halogen or alkyl of 1 to 2 carbon atoms;
R₂ is hydrogen, chlorine, bromine, straight or branched alkyl of 1 to 3 carbon atoms, ω-hydroxyalkyl of 1 to 3 carbon atoms, cycloalkyl of 3 to 6 carbon atoms, tetrahydrofuranyl, tetrahydropyranyl, N-methyl-piperidyl or thienyl; and
R₃ is hydrogen, fluorine, chlorine or bromine;
which comprises the steps of
(a) reducing a compound of the formula

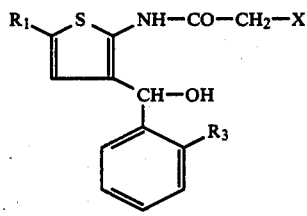

wherein
R₁ and R₃ have the meanings defined above, and
X is halogen, amino or carboxylic acyloxy,
with sodium borohydride in dimethylformamide or dimethylacetamide at temperatures between 0° and +10° C. to form a corresponding carbinol of the formula

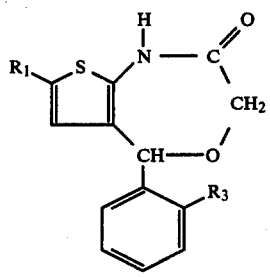

wherein R₁, R₃ and X have the meanings defined above;
(b) treating the carbinol, optionally after conversion of the amino group into a halogen atom or after splitting off the acyl group, with a cyclization agent to form a carbonyl compound of the formula

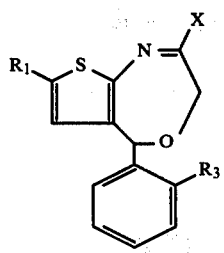

wherein R₁ and R₃ have the meanings defined above;
(c) converting the carbonyl group into the mercapto, a lower alkoxy or an alkylmercapto group or into a halogen atom by conventional methods to form a compound of the formula

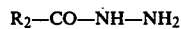

wherein
R₁ and R₃ have the meanings defined above, and
X is Sh—, lower alkoxy, alkylmercapto or halogen;
(d) reacting the compound thus obtained with a compound of the formula

R₂—CO—NH—NH₂ wherein R₂ has the meanings previously defined except chlorine and bromine;

(e) optionally chlorinating or brominating a compound of the formula

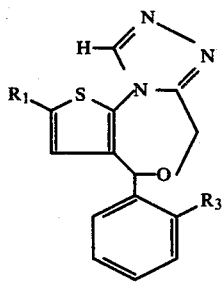

thus obtained, wherein R₁ and R₃ have the meanings defined above, with a chlorinating or brominating agent;

(f) cleaving the oxazepine ring of the compound at the oxygen atom by treating it with a strong hydrohalic acid;

(g) extracting the resulting hydrohalide of a compound of the formula

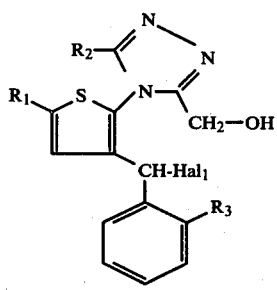

wherein
R₁ through R₃ have the meanings defined above and
Hal₁ is halogen, with a water-immiscible solvent;

(h) admixing the residue with a phosphorus halide or sulfur halide;

(i) reacting the resulting dihalo compound of the formula

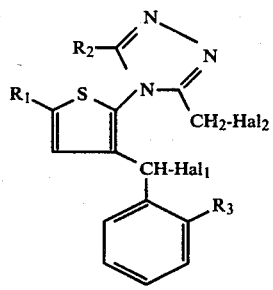

wherein
R₁ through R₃ have the meanings defined above, and
Hal₁ and Hal₂ are halogen,
with ammonia or an ammonia-releasing substance to form a compound of the formula

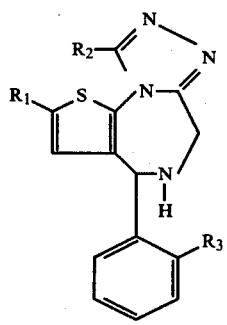

wherein R₁ through R₃ have the meanings defined above; and (j) dehydrogenating the resulting compound with a halogen or a compound of the higher oxidation stage of chromium or manganese.

2. The process of claim 1, where the cyclization agent in step (b) is sodium isopropylate or sodium tert. butylate.

3. The process of claim 1, where the dehydrogenation in step (j) is carried out with a halogen as the dehydrogenation agent.

4. The process of claim 1, where the dehydrogenation in step (j) is carried out with a compound of the higher oxidation stages of chromium or manganese as the dehydrogenation agent.

5. The process of claim 4, wherein the dehydrogenation agent is an alkai metal dichromate.

6. The process of claim 4, where the dehydrogenation agent is an alkali metal permanganate.

* * * * *

UNITED STATES PATENT AND TRADEMARK OFFICE
CERTIFICATE OF CORRECTION

PATENT NO. : 4,201,712
DATED : May 6, 1980
INVENTOR(S) : KARL-HEINZ WEBER ET AL.

It is certified that error appears in the above-identified patent and that said Letters Patent are hereby corrected as shown below:

Column 1, line 36: "chloride" should read -- chlorine --.

Column 17, claim 1: The portion of the first structural formula which reads

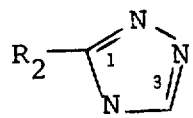

should read

-- 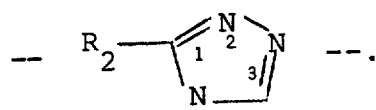 --.

Signed and Sealed this

Eleventh Day of November 1980

[SEAL]

Attest:

SIDNEY A. DIAMOND

Attesting Officer

Commissioner of Patents and Trademark